(12) United States Patent
Schenck

(10) Patent No.: US 8,121,704 B2
(45) Date of Patent: Feb. 21, 2012

(54) LEAKAGE-RESISTANT TISSUE TREATMENT APPARATUS AND METHODS OF USING SAME

(75) Inventor: Alan Schenck, Sunnyvale, CA (US)

(73) Assignee: Thermage, Inc., Hayward, CA (US)

( * ) Notice: Subject to any disclaimer, the term of this patent is extended or adjusted under 35 U.S.C. 154(b) by 916 days.

(21) Appl. No.: 12/142,104

(22) Filed: Jun. 19, 2008

(65) Prior Publication Data

US 2009/0318850 A1    Dec. 24, 2009

(51) Int. Cl.
*A61F 2/00* (2006.01)
(52) U.S. Cl. ............... 607/101; 607/99; 606/41
(58) Field of Classification Search ............ 607/96–105; 606/9, 22, 29, 32–53
See application file for complete search history.

(56) References Cited

U.S. PATENT DOCUMENTS

| | | |
|---|---|---|
| 3,948,269 A | 4/1976 | Zimmer |
| 5,281,213 A | 1/1994 | Milder et al. |
| 5,348,554 A | 9/1994 | Imran et al. |
| 5,423,811 A | 6/1995 | Imran et al. |
| 5,697,927 A | 12/1997 | Imran et al. |
| 5,735,846 A | 4/1998 | Panescu et al. |
| 5,755,753 A | 5/1998 | Knowlton |
| 5,871,524 A | 2/1999 | Knowlton |
| 5,919,219 A | 7/1999 | Knowlton |
| 5,948,011 A | 9/1999 | Knowlton |
| 6,035,238 A | 3/2000 | Ingle et al. |
| 6,059,780 A | 5/2000 | Gough et al. |
| 6,081,749 A | 6/2000 | Ingle et al. |
| 6,139,569 A | 10/2000 | Ingle et al. |
| 6,216,704 B1 | 4/2001 | Ingle et al. |
| 6,236,891 B1 | 5/2001 | Ingle et al. |

(Continued)

FOREIGN PATENT DOCUMENTS

WO    9916502    4/1999

(Continued)

OTHER PUBLICATIONS

Schenck, "Apparatus and Methods for Cooling a Treatment Apparatus Configured to Non-Invasively Deliver Electromagnetic Energy to a Patient's Tissue", U.S. Appl. No. 11/952,649, filed Dec. 7, 2007.

(Continued)

*Primary Examiner* — Linda Dvorak
*Assistant Examiner* — Adam Avigan
(74) *Attorney, Agent, or Firm* — Wood, Herron & Evans, LLP

(57) ABSTRACT

Apparatus and methods for treating skin conditions that deliver high frequency energy to a patient's tissue. The apparatus has a treatment tip configured to be removably coupled with a handpiece and a conduit inside the handpiece. The treatment tip includes an electrode configured to deliver the high frequency energy to a region of the tissue, a channel for circulating heat transfer fluid proximate to the electrode, and an inlet passage to the channel. The conduit includes a tubular sidewall with a lumen used to transfer the heat transfer fluid from the handpiece to the inlet passage of the treatment tip. When the treatment tip is coupled to the handpiece, a septum covering the inlet passage is configured to be pierced by the conduit to define an opening for coupling the conduit with the inlet passage. When the treatment tip is removed from the handpiece, the septum substantially seals the opening.

18 Claims, 6 Drawing Sheets

U.S. PATENT DOCUMENTS

| | | |
|---|---|---|
| 6,241,753 B1 | 6/2001 | Knowlton |
| 6,283,987 B1 | 9/2001 | Laird et al. |
| 6,311,090 B1 | 10/2001 | Knowlton |
| 6,322,584 B2 | 11/2001 | Ingle et al. |
| 6,350,276 B1 | 2/2002 | Knowlton |
| 6,377,854 B1 | 4/2002 | Knowlton |
| 6,377,855 B1 | 4/2002 | Knowlton |
| 6,381,497 B1 | 4/2002 | Knowlton |
| 6,381,498 B1 | 4/2002 | Knowlton |
| 6,387,380 B1 | 5/2002 | Knowlton |
| 6,405,090 B1 | 6/2002 | Knowlton |
| 6,413,255 B1 | 7/2002 | Stern |
| 6,425,912 B1 | 7/2002 | Knowlton |
| 6,430,446 B1 | 8/2002 | Knowlton |
| 6,438,424 B1 | 8/2002 | Knowlton |
| 6,453,202 B1 | 9/2002 | Knowlton |
| 6,461,378 B1 | 10/2002 | Knowlton |
| 6,470,216 B1 | 10/2002 | Knowlton |
| 6,480,746 B1 | 11/2002 | Ingle et al. |
| 6,524,308 B1 | 2/2003 | Muller et al. |
| 6,533,780 B1 | 3/2003 | Laird et al. |
| 6,558,381 B2 | 5/2003 | Ingle et al. |
| 6,572,639 B1 | 6/2003 | Ingle et al. |
| 6,652,565 B1 * | 11/2003 | Shimada et al. .............. 607/105 |
| 6,702,808 B1 | 3/2004 | Kreindel |
| 6,976,492 B2 | 12/2005 | Ingle et al. |
| 6,997,923 B2 | 2/2006 | Anderson et al. |
| 7,006,874 B2 | 2/2006 | Knowlton et al. |
| 7,022,121 B2 * | 4/2006 | Stern et al. ...................... 606/41 |
| 7,090,670 B2 | 8/2006 | Sink |
| 7,115,123 B2 | 10/2006 | Knowlton et al. |
| 7,141,049 B2 | 11/2006 | Stern et al. |
| 7,164,942 B2 | 1/2007 | Avrahami et al. |
| 7,189,230 B2 | 3/2007 | Knowlton |
| D544,955 S | 6/2007 | Carson et al. |
| 7,229,436 B2 | 6/2007 | Stern et al. |
| 7,257,450 B2 | 8/2007 | Auth et al. |
| 7,267,675 B2 | 9/2007 | Stern et al. |
| 7,452,358 B2 | 11/2008 | Stern et al. |
| 7,473,251 B2 | 1/2009 | Knowlton et al. |
| 7,473,252 B2 | 1/2009 | Barry |
| 7,481,809 B2 | 1/2009 | Stern et al. |
| 7,494,488 B2 | 2/2009 | Weber |
| 2003/0178032 A1 | 9/2003 | Ingle et al. |
| 2003/0216719 A1 | 11/2003 | Debenedictis et al. |
| 2004/0082940 A1 | 4/2004 | Black et al. |
| 2005/0049582 A1 | 3/2005 | DeBenedictis et al. |
| 2005/0171582 A1 | 8/2005 | Matlock |
| 2006/0009750 A1 | 1/2006 | Altshuler et al. |
| 2006/0122668 A1 | 6/2006 | Anderson et al. |
| 2006/0149343 A1 | 7/2006 | Altshuler et al. |
| 2006/0206103 A1 | 9/2006 | Altshuler et al. |
| 2006/0206179 A1 | 9/2006 | Black |

FOREIGN PATENT DOCUMENTS

| | | |
|---|---|---|
| WO | 200053113 | 9/2000 |
| WO | 0100269 | 1/2001 |
| WO | 03053266 | 3/2003 |
| WO | 03065915 | 8/2003 |
| WO | 03065916 | 8/2003 |
| WO | 03086217 | 10/2003 |
| WO | 2004086943 | 10/2004 |
| WO | 2004087253 | 10/2004 |
| WO | 2004088700 | 10/2004 |
| WO | 2004089185 | 10/2004 |
| WO | 2004089186 | 10/2004 |
| WO | 2004089459 | 10/2004 |
| WO | 2004089460 | 10/2004 |
| WO | 2004090939 | 10/2004 |
| WO | 2004105861 | 12/2004 |

OTHER PUBLICATIONS

Schenck, "Leakage-Resistant Tissue Treatment Apparatus and Methods of Using Such Tissue Treatment Apparatus", U.S. Appl. No. 12/142,020, filed Jun. 19, 2008.

Schenck, "Methods and Apparatus for Predictively Controlling the Temperature of a Coolant Delivered to a Treatment Device", U.S. Appl. No. 12/110,384, filed Apr. 28, 2008.

* cited by examiner

LEAKAGE-RESISTANT TISSUE TREATMENT APPARATUS AND METHODS OF USING SAME

FIELD OF THE INVENTION

The invention generally relates to apparatus and methods for treating tissue with high frequency energy and, more particularly, relates to treatment apparatus and methods for treating tissue with high frequency energy that include liquid-mediated tissue cooling and leakage control mechanisms for the heat transfer fluid used in the liquid-mediated tissue cooling.

BACKGROUND OF THE INVENTION

Energy delivery devices that can non-invasively treat tissue are extensively used to therapeutically treat numerous diverse skin conditions. Among other uses, non-invasive energy delivery devices may be used to tighten loose skin to make a patient appear younger, remove skin spots or hair, or kill bacteria. Such non-invasive energy delivery devices emit electromagnetic energy in different regions of the electromagnetic spectrum for tissue treatment.

High frequency treatment devices, such as radio-frequency (RF)-based devices, may be used to treat skin tissue non-ablatively and non-invasively by passing high frequency energy through a surface of the skin to underlying tissue, while actively cooling the skin to prevent damage to a region of the tissue near the skin surface. The high frequency energy heats the tissue beneath the cooled region to a temperature sufficient to denature collagen, which causes the collagen to contract and shrink and, thereby, tighten the treated tissue. Treatment with high frequency energy also causes a mild inflammation. The inflammatory response of the treated tissue causes new collagen to be generated over time (between three days and six months following treatment), which results in further tissue contraction.

Modern high frequency treatment devices employ a handpiece, a treatment tip coupled with the handpiece, and a high frequency generator connected with electrodes in the treatment tip by the handpiece. Conventional electrodes consist of a pattern of metallic features carried on a flexible electrically insulating substrate, such as a thin film of polyimide. The substrate contacts the patient's skin surface during treatment. The temperature of the treatment tip, which is measured by temperature sensors carried on the treatment tip, is correlated with the temperature of the patient's skin.

Treatment tips are frequently intended for single patient use and, therefore, non-reusable. As a result, the disposable treatment tips are designed to be temporarily installed onto the nose of the reusable handpiece. Upon installation onto the handpiece nose, one or more latches lock the treatment tip in the proper position. After the conclusion of the patient treatment, the doctor or treatment technician unlatches the treatment tip and removes it from the handpiece to be discarded.

The treatment tip is cooled with a heat transfer fluid for the purpose of cooling the tissue region proximate to the skin surface that is in a contacting relationship with the substrate carrying the one or more electrodes. The superficial cooling protects outer layers of tissue and regulates the treatment depth. One approach for supplying heat transfer fluid to the treatment tip is a closed-loop cooling system that circulates the heat transfer fluid through the treatment tip. When the treatment tip and handpiece are united together, pathways are established between the treatment tip and handpiece for the transfer of fluid to and the draining of fluid from the treatment tip.

When the treatment tip is initially united with the handpiece, the pathways from the handpiece to the treatment tip should be free of leakage. The separate pathways permit the heat transfer fluid to flow from the handpiece to the treatment tip and then return from the treatment tip back to the handpiece after circulation through the treatment tip. When the treatment tip is separated from the handpiece following a patient treatment, the continuity of the pathways is severed. The portions of the severed pathways in the handpiece are unblocked, which may permit the heat transfer fluid to leak or drip from the handpiece. In addition, the portions of the severed pathways in the treatment tip are also unblocked, which may cause heat transfer fluid to leak from the treatment tip before disposal.

What is needed, therefore, are apparatus and methods for controlling the escape of heat transfer fluid from the treatment tip when the treatment tip is removed from the handpiece.

SUMMARY OF THE INVENTION

The invention is generally directed to treatment apparatus and methods that deliver high frequency energy to tissue underlying a skin surface during non-invasive tissue treatments. The treatment apparatus delivers a fluid, such as a heat transfer fluid, from a handpiece to a treatment tip. The fluid may be returned from the treatment tip to the handpiece to define closed loop circulation.

In one embodiment, the apparatus includes a treatment tip configured to be removably coupled with a handpiece and a conduit inside the handpiece. The treatment tip includes an electrode configured to deliver the high frequency energy to a region of the tissue, a channel for circulating heat transfer fluid proximate to the electrode, and an inlet passage to the channel. The conduit includes a tubular sidewall with a lumen configured to be coupled with the inlet passage for transferring the heat transfer fluid from the handpiece to the inlet passage of the treatment tip. A septum covers the inlet passage and, when the treatment tip is coupled to the handpiece, is configured to be pierced by the conduit to define an opening for coupling the first conduit with the inlet passage. When the treatment tip is removed from the handpiece to decouple the conduit from the inlet passage, the septum substantially seals the first opening.

In another embodiment, a method is provided for operating a tissue treatment apparatus to treat tissue located beneath a skin surface with high frequency energy delivered from an electrode. The method includes attaching a treatment tip carrying the electrode to a handpiece to establish a fluid connection between a lumen of a conduit in the handpiece and an inlet passage in the treatment tip. When attaching the treatment tip to the handpiece to establish the fluid connection, the conduit pierces a septum to define an opening permitting the conduit to be coupled in fluid communication with the inlet passage. The method further includes transferring heat transfer fluid through the lumen of the conduit to the treatment tip, and delivering the high frequency energy from the electrode to a region of the tissue to perform a tissue treatment.

DETAILED DESCRIPTION

Figure 1:
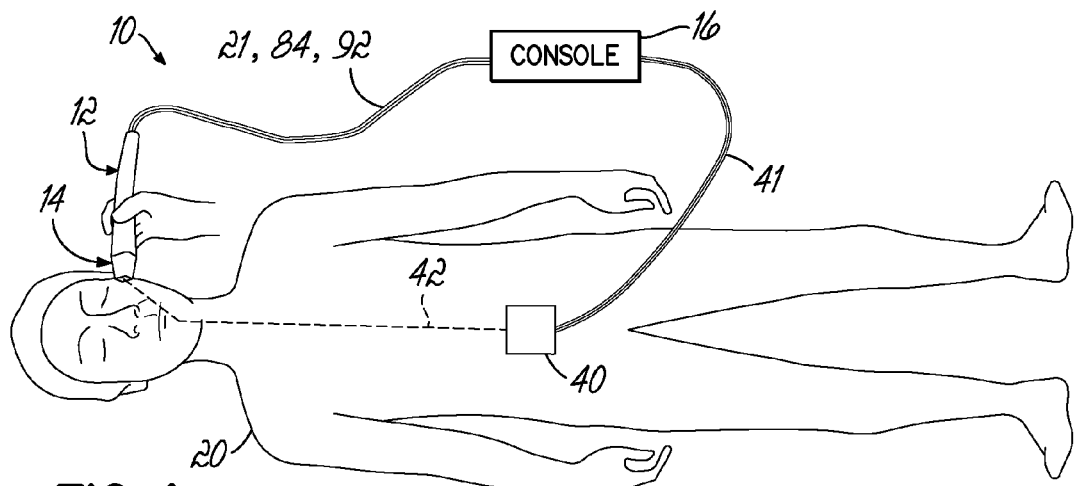
FIG. 1 is a diagrammatic view of a treatment system with a handpiece, a treatment tip, and a console in accordance with an embodiment of the invention

With reference to FIGS. 1-4, a treatment apparatus 10 includes a handpiece 12, a treatment tip 14 coupled in a removable and releasable manner with the handpiece 12, a console generally indicated by reference numeral 16, and a system controller 18. The system controller 18, which is incorporated into the console 16, controls the global operation of the different individual components of the treatment apparatus 10. Under the control of the system controller 18 and an operator's interaction with the system controller 18 at the console 16, the treatment apparatus 10 is adapted to selectively deliver electromagnetic energy in a high frequency band of the electromagnetic spectrum, such as the radiofrequency (RF) band to non-invasively heat a region of a patient's tissue to a targeted temperature range. The elevation in temperature may produce a desired treatment, such as removing or reducing wrinkles and otherwise tightening the skin to thereby improve the appearance of a patient 20 receiving the treatment. In alternative embodiments, the treatment apparatus 10 may be configured to deliver energy in the infrared band, microwave band, or another high frequency band of the electromagnetic spectrum, rather than energy in the RF band, to the patient's tissue.

The treatment tip 14 carries an energy delivery member in the representative form of a treatment electrode 22. The treatment electrode 22 is electrically coupled by a set of conductors 21 with a generator 38 configured to generate the electromagnetic energy used in the patient's treatment. In a representative embodiment, the treatment electrode 22 may have the form of a region 26 of an electrical conductor carried on an electrically-insulating substrate 28 composed of a dielectric material. In one embodiment, the substrate 28 may comprise a thin flexible base polymer film carrying the conductor region 26 and thin conductive (e.g., copper) traces or leads 24 on the substrate 28 that electrically couple the conductor region 26 with contact pads 25. The base polymer film may be, for example, polyimide or another material with a relatively high electrical resistivity and a relatively high thermal conductivity. The conductive leads 24 may contain copper or another material with a relatively high electrical conductivity. Instead of the representative solid conductor region 26, the conductor region 26 of treatment electrode 22 may include voids or holes unfilled by the conductor to provide a perforated appearance or, alternatively, may be segmented into plural individual electrodes that can be individually powered by the generator 38.

In one specific embodiment, the treatment electrode 22 may comprise a flex circuit in which the substrate 28 consists of a base polymer film and the conductor region 26 consists of a patterned conductive (i.e., copper) foil laminated to the base polymer film. In another specific embodiment, the treatment electrode 22 may comprise a flex circuit in which the conductor region 26 consists of patterned conductive (i.e., copper) metallization layers directly deposited the base polymer film by, for example, a vacuum deposition technique, such as sputter deposition. In each instance, the base polymer film constituting substrate 28 may be replaced by another non-conductive dielectric material and the conductive metallization layers or foil constituting the conductor region 26 may contain copper. Flex circuits, which are commonly used for flexible and high-density electronic interconnection applications, have a conventional construction understood by a person having ordinary skill in the art.

The substrate 28 includes a contact side 32 that is placed into contact with the skin surface of the patient 20 during treatment and a non-contact side 34 that is opposite to the contact side 32. The conductor region 26 of the treatment electrode 22 is physically carried on non-contact side 34 of the substrate 28. In the representative arrangement, the substrate 28 is interposed between the conductor region 26 and the treated tissue such that, during the non-invasive tissue treatment, electromagnetic energy is transmitted from the conductor region 26 through the thickness of the substrate 28 by capacitively coupling with the tissue of the patient 20.

When the treatment tip 14 is physically engaged with the handpiece 12, the contact pads 25 face toward the handpiece 12 and are electrically coupled with electrical contacts (not shown), such as pogo pin contacts, inside the handpiece 12. These electrical contacts are electrically coupled with insulated and shielded conductors 21 that extend exteriorly of the handpiece 12 to a generator 38 at the console 16. The generator 38, which has the form of a high frequency power supply, is equipped with an electrical circuit (not shown) operative to generate high frequency electrical current, typically in the radio-frequency (RF) region of the electromagnetic spectrum. The operating frequency of generator 38 may advantageously be in the range of several hundred kHz to about twenty (20) MHz to impart a therapeutic effect to treat target tissue beneath a patient's skin surface. The circuit in the generator 38 converts a line voltage into drive signals having an energy content and duty cycle appropriate for the amount of power and the mode of operation that have been selected by the clinician, as understood by a person having ordinary skill in the art. In one embodiment, the generator 38 is a 400-watt, 6.78 MHz high frequency generator.

A non-therapeutic passive or return electrode 40, which is electrically coupled with the generator 38, is physically attached to a site on the body surface of the patient 20, such as the patient's lower back. During treatment, high frequency current flows from the treatment electrode 22 through the treated tissue and the intervening bulk of the patient 20 to the return electrode 40 and then through conductors inside a return cable 41 to define a closed circuit or current path 42. Because of the relatively large surface area of the return electrode 40 in contact with the patient 20, the current density flowing from the patient 20 to the return electrode 40 is relatively low in comparison with the current density flowing from the treatment electrode 22 to the patient 20. As a result, the return electrode 40 is non-therapeutic because negligible heating is produced at its attachment site to the patient 20.

High frequency electrical current flowing between the treatment electrode 22 and the patient 20 is maximized at the skin surface and underlying tissue region adjacent to the treatment electrode 22 and, therefore, delivers a therapeutic effect to the tissue region near the treatment site.

Figure 3:
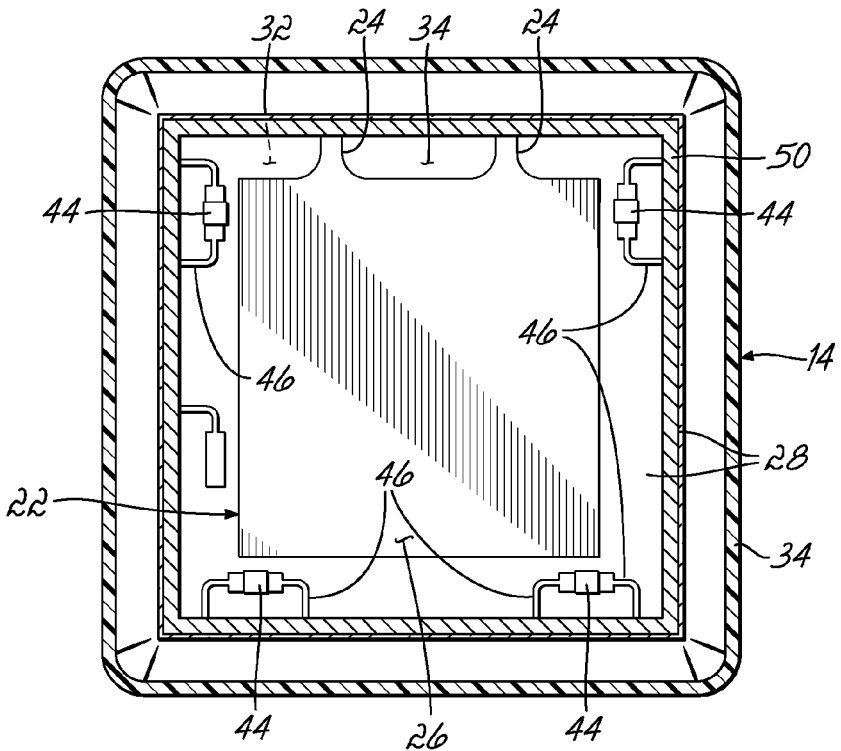
FIG. 3 is a rear view of the assembled treatment tip taken generally along line 3-3 in FIG. 2 showing the electrode and temperature sensors.

As best shown in FIG. 3, the treatment tip 14 includes temperature sensors 44, such as thermistors or thermocouples, that are located on the non-contact side 34 of the substrate 28 that is not in contact with the patient's skin surface. Typically, the temperature sensors 44 are arranged about the perimeter of the conductor region 26 of the treatment electrode 22. Temperature sensors 44 are constructed to detect the temperature of the treatment electrode 22 and/or treatment tip 14, which may be representative of the temperature of the treated tissue. Each of the temperature sensors 44 is electrically coupled by conductive leads 46 with one or more of the contact pads 25, which are used to supply direct current (DC) voltages from the system controller 18 through the shielded conductors 21 to the temperature sensors 44.

With continued reference to FIGS. 1-4, the system controller 18 regulates the power delivered from the generator 38 to the treatment electrode 22 and otherwise controls and supervises the operational parameters of the treatment apparatus 10. The system controller 18 may include user input devices to, for example, adjust the applied voltage level of generator 38. The system controller 18 includes a processor, which may be any suitable conventional microprocessor, microcontroller or digital signal processor, executing software to implement control algorithms for the operation of the generator 38. System controller 18, which may also include a nonvolatile memory (not shown) containing programmed instructions for the processor, may be optionally integrated into the generator 38. System controller 18 may also communicate, for example, with a nonvolatile memory carried by the handpiece 12 or by the treatment tip 14. The system controller 18 also includes circuitry for supplying the DC voltages and circuitry that relates changes in the DC voltages to the temperature detected by the temperature sensors 44, as well as temperature sensors 90 and 88.

Figure 8:
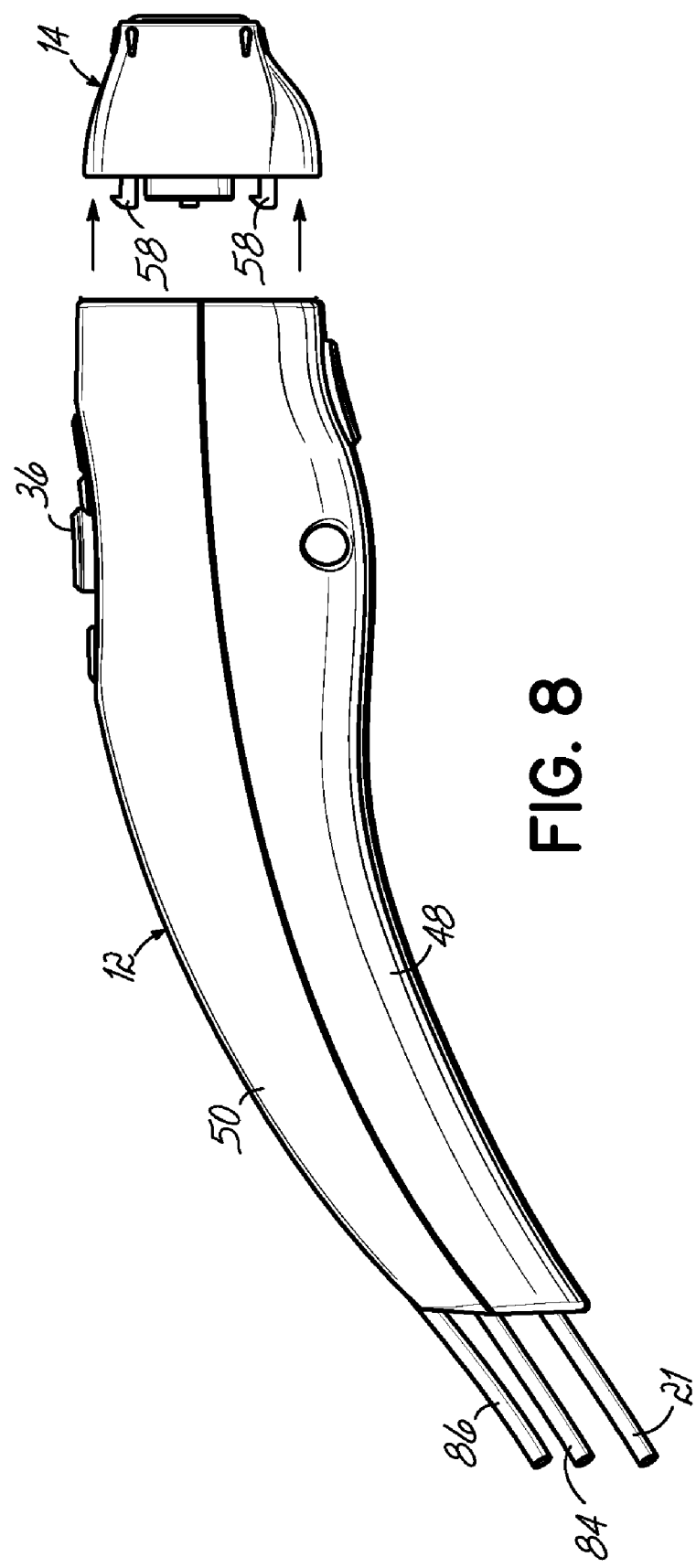
FIG. 8 is a perspective view of the handpiece and treatment tip of FIG. 2 in which the treatment tip is shown separated from the handpiece.

With specific reference to FIG. 8, the handpiece 12 is constructed from a body 48 and a cover 50 that is assembled with conventional fasteners with the body 48. The assembled handpiece 12 has a smoothly contoured shape suitable for manipulation by a clinician to maneuver the treatment tip 14 and treatment electrode 22 to a location proximate to the skin surface and, typically, in a contacting relationship with the skin surface. An activation button 36, which is accessible to the clinician from the exterior of the handpiece 12, is depressed for closing a switch that energizes the treatment electrode 22 and, thereby, delivers high frequency energy over a short delivery cycle to treat the target tissue. Releasing the activation button 36 opens the switch to discontinue the delivery of high frequency energy to the patient's skin surface and underlying tissue. After the treatment of one site is concluded, the handpiece 12 is manipulated to position the treatment tip 14 near a different site on the skin surface for another delivery cycle of high frequency energy delivery to the patient's tissue.

Figure 4:
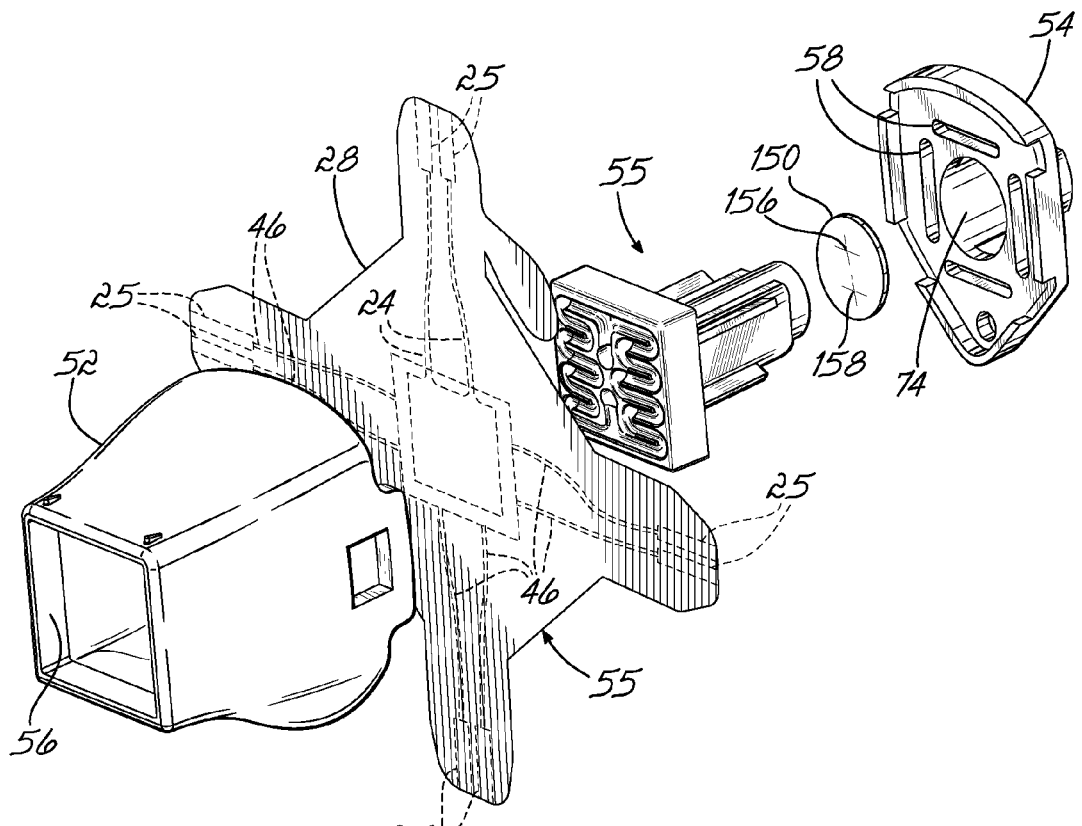
FIG. 4 is an exploded view of the treatment tip of FIG. 2 in which the treatment electrode is shown in an unfolded condition.
Figure 5:
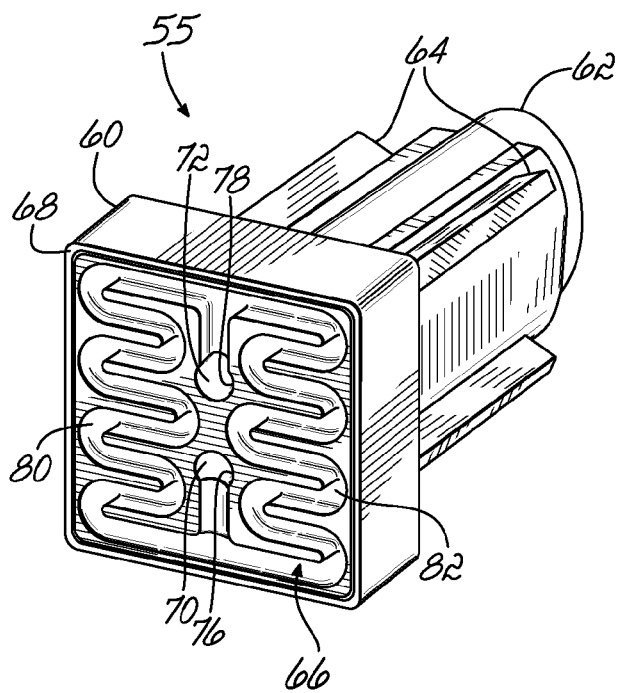
FIG. 5 is a front perspective view of a manifold body located inside the treatment tip of FIG. 4.
Figure 6:
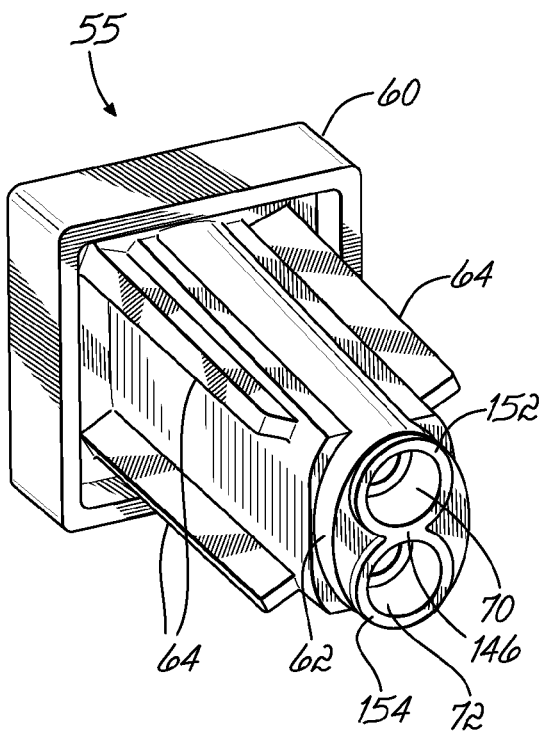
FIG. 6 is a rear perspective view of the manifold body of FIG. 5.

With reference to FIGS. 4-6, the treatment tip 14 includes a rigid outer shell 52, a rear cover 54 that is coupled with an open rearward end of the outer shell 52, and a manifold body 55 disposed inside an enclosure or housing inside the outer shell 52. A portion of the substrate 28 overlying the conductor region 26 of the treatment electrode 22 is exposed through a window 56 defined in a forward open end of the outer shell 52. The substrate 28 is wrapped or folded about the manifold body 55. A hooked prong 58 (FIGS. 7, 9), which projects from the rear cover 54, is captured by a lip on the handpiece 12 during installation of the treatment tip 14.

As best shown in FIGS. 4 and 5, the manifold body 55, which may be formed from an injection molded polymer resin, includes a front section 60, a stem 62 projecting rearwardly from the front section 60, and ribs 64 on the stem 62 used to position the manifold body 55 inside the outer shell 52. The front section 60 of the manifold body 55 includes a channel 66 that, in the assembly constituting treatment tip 14, underlines the conductor region 26 of the treatment electrode 22. The shape of the front section 60 corresponds with the shape of the window 56 in the outer shell 52. The substrate 28 of the treatment electrode 22 is bonded with a rim 68 of the manifold body 55 to provide a fluid seal that confines heat transfer fluid 94 flowing in the channel 66. The area inside the rim 68 is approximately equal to the area of the conductor region 26 of treatment electrode 22. Channel 66 includes convolutions that are configured to optimize the residence time of the heat transfer fluid 94 in channel 66, which may in turn optimize the heat transfer between the heat transfer fluid 94 and the treatment electrode 22.

An inlet bore or passage 70 and an outlet bore or passage 72 extend through the stem 62 of the manifold body 55. The inlet passage 70 and outlet passage 72 are rearwardly accessible through an oval-shaped slot 74 defined in the rear cover 54. The inlet passage 70 intersects the channel 66 at an inlet 76 to the channel 66 and the outlet passage 72 intersects the channel 66 at an outlet 78 from the channel 66. The channel 66 is split into two channel sections 80, 82 so that fluid flow in the channel 66 diverges away in two separate streams from the inlet 76 and converges together to flow into the outlet 78. Fluid pressure causes the heat transfer fluid 94 to flow from the inlet 76 through the two channel sections 80, 82 to the outlet 78 and into the outlet passage 72.

With reference to FIGS. 2 and 4-6, fluid connections are established with the inlet passage 70 and the outlet passage 72 to establish the closed circulation loop and permit fluid flow to the channel 66 in the manifold body 55 when the treatment tip 14 is mated with the handpiece 12. Specifically, the inlet passage 70 to the manifold body 55 is coupled with a supply line 86 in the form of an inlet conduit or tube. The outlet passage 72 from the manifold body 55 is coupled with a return line 84 in the form of a fluid conduit or tube. The return line 84 and the supply lines 86 extend out of the handpiece 12 and are routed to the console 16. Structure facilitating the establishment of fluid-tight connections is described in detail hereinbelow.

Figure 2:
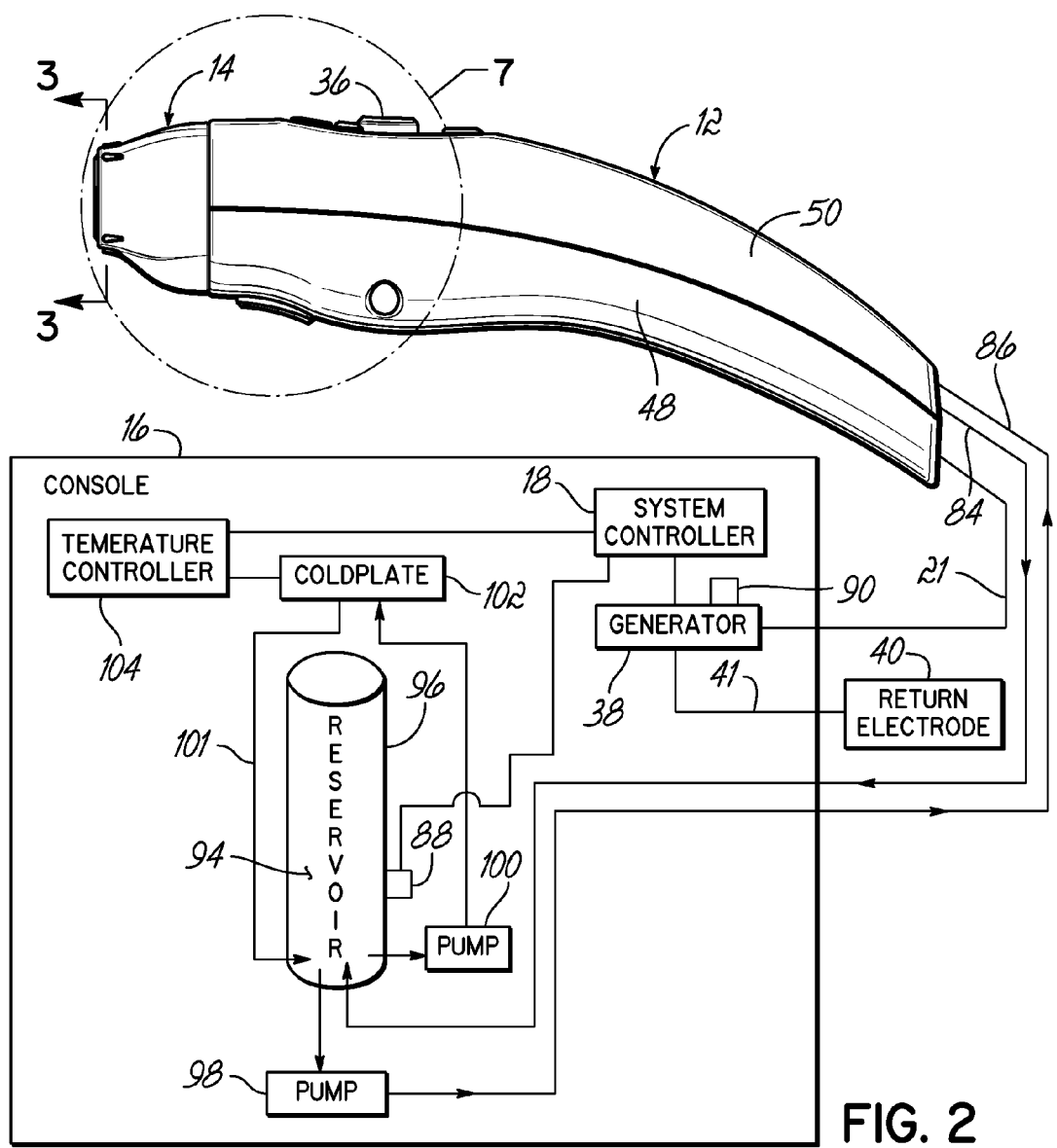
FIG. 2 is a diagrammatic view of the handpiece, treatment tip, and console of FIG. 1 showing a closed-loop cooling system of the treatment system.

With reference to FIG. 2, the treatment apparatus 10 is equipped with a closed loop cooling system that includes the manifold body 55 located inside the treatment tip 14. The closed loop cooling system further includes a reservoir 96 holding a volume of a heat transfer fluid 94 and a pump 98, which may be a diaphragm pump, that continuously pumps a stream of the heat transfer fluid 94 from an outlet of the reservoir 96 through the supply line 86 to the manifold body 55 in the treatment tip 14. The manifold body 55 is coupled in fluid communication with the reservoir 96 by the return line 84. The return line 84 conveys the heat transfer fluid 94 from the treatment tip 14 back to the reservoir 96 to complete the circulation loop.

Heat generated in the treatment tip 14 by energy delivery from the treatment electrode 22 and heat transferred from the patient's skin and an underlying depth of heated tissue is conducted through the substrate 28 and treatment electrode 22. The heat is absorbed by the circulating heat transfer fluid 94 in the channel 66 of the manifold body 55, which lowers the temperature of the treatment electrode 22 and substrate 28 and, thereby, cools the patient's skin and the underlying depth of heated tissue. The contact cooling, at the least, assists in regulating the depth over which the tissue is heated to a therapeutic temperature by the delivered electromagnetic energy.

The heat transfer fluid 94 stored in the reservoir 96 is chilled by a separate circulation loop 101 that pumps heat transfer fluid 94 from the reservoir 96 through separate supply and return lines to a coldplate 102. A pump 100, which may be a centrifugal pump, pumps the heat transfer fluid 94 under pressure from the reservoir 96 to the coldplate 102. In a representative embodiment, the coldplate 102 may be a liquid-to-air heat exchanger that includes a liquid heat sink with a channel (not shown) for circulating the heat transfer fluid 94, a thermoelectric module (not shown), and an air-cooled heat sink (not shown).

A temperature controller 104 inside the console 16 is electrically coupled with the coldplate 102 and is also electrically coupled with the system controller 18. The system controller 18, which is electrically coupled with a temperature sensor 88 used to measure the heat transfer fluid temperature in the reservoir 96, supplies temperature control signals to the temperature controller 104 in response to the measured heat transfer fluid temperature. Under the feedback control, the temperature controller 104 reacts to the control temperature communicated from the temperature sensor 88 to control the operation of the coldplate 102 and, thereby, regulate the temperature of the heat transfer fluid 94 in the reservoir 96.

With reference to FIGS. 4 and 7-9, the handpiece 12 includes a pair of rigid tubes 110, 112 with respective tips 114, 116 that project outwardly from a flow part 118. The flow part 118 conceals the portions of the rigid tubes 110, 112 located inside the handpiece 12. The rigid tubes 110, 112 extend through respective openings penetrating through the flow part 118 and have lumens 111, 113 that are respectively coupled inside the handpiece 12 with a pair of flexible conduits or lines 120, 122.

A flow control valve in the representative form of a pinch valve, generally indicated by reference numeral 124, is located inside the handpiece 12. The pinch valve 124 includes a pin 126, a movable member in the form of a ram or plunger 128 that is mechanically coupled with the pin 126 to form an assembly, a stationary member in the form of an anvil body 130 on the flow part 118, and an actuator in the representative form of a coil spring 132 that is configured to apply a biasing force to the plunger 128. A forward end 125 of the pin 126 is centrally located between the tips 114, 116 of the rigid tubes 110, 112 and, inside the handpiece 12, the remainder of the pin 126 is centrally located between the rigid tubes 110, 112 and the flexible lines 120, 122. The anvil body 130 includes a spaced-apart pair of contoured contact or pinch surfaces 134, 136. One of the flexible lines 120 is located between a contact or pinch surface 138 of plunger 128 and pinch surface 134 on the anvil body 130. The other flexible line 122 is located between a contact or pinch surface 140 of plunger 128 and pinch surface 136 on the anvil body 130.

The pinch valve 124 has a first closed position (FIGS. 8, 9) in which the flexible lines 120, 122 are respectively compressed between the pinch surfaces 134, 136 on anvil body 130 and the pinch surfaces 138, 140 on plunger 128. The material forming the flexible lines 120, 122 is sufficiently compliant to the compressive force or pressure from the pinching action so that the respective sidewalls collapse inwardly to totally or partially occlude a lumen 142 of flexible line 120 and a lumen 144 of flexible line 122. In a closed position, heat transfer fluid 94 is substantially or completely occluded by the pinch valve 124 from flowing through the flexible lines 120, 122 to an extent sufficient to reduce or eliminate fluid leakage from the outlets of the rigid tubes 110, 112. The closed position occurs when the treatment tip 14 is removed from the handpiece 12.

The rigid tubes 110, 112, which are relatively short in comparison with the flexible lines 120, 122, may be formed from a stainless steel. In contrast, the flexible lines 120, 122 are formed from a polymer or an elastomeric material, like a silicone rubber, that is significantly more flexible (has a greater ability to bend) than the material forming the rigid tubes 110, 112. In other words, the flexible lines 120, 122 are formed from a material having a significantly lower shear modulus or modulus of rigidity than a material forming the rigid tubes 110, 112.

The flexible lines 120, 122 distort slightly to permit the ends of the flexible lines 120, 122 to be slipped over respective lengths of the rigid tubes 110, 112 and grip the rearward ends of the rigid tubes 110, 112 after installation to provide a fluid-tight seal. Flexible line 120 has a tubular sidewall 121 composed of a material with sufficient flexibility to at least partially occlude the enclosed lumen 142 by reducing the cross-sectional area for fluid flow when a compressive force is applied between pinch surface 138 of plunger 128 and pinch surface 134 on the anvil body 130 of the pinch valve 124. The occlusion, which controls the flow of fluid through the lumen 142, causes deformation that at least partially collapses the lumen 142. Similarly, flexible line 122 has a tubular sidewall 123 composed of a material with sufficient flexibility to at least partially occlude the enclosed lumen 144 by reducing the cross-sectional area for fluid flow when a compressive force is applied between pinch surface 140 of plunger 128 and pinch surface 136 on the anvil body 130 of the pinch valve 124. The occlusion, which controls the flow of fluid through the lumen 144, causes deformation that at least partially collapses the lumen 144. The deformation of the tubular sidewalls 121, 123 is primarily elastic in that the tubular sidewalls 121, 123 return to substantially their original shape and cross-sectional area when the compressive force is removed.

In the closed position, respective columns of residual heat transfer fluid 94 may remain inside the rigid tubes 110, 112, as well as inside the portion of the flexible lines 120, 122 between the pinch surfaces 134, 136, 138, 140 and the rigid tubes 110, 112. Although not wishing to be bound by theory, the columns may remain static and resident inside the handpiece 12 until another treatment tip 14 is installed, which implies that the effective flow rate is zero milliliters per minute.

The pinch valve 124 has an open position (FIGS. 4, 7) in which the pinch surfaces 138, 140 on plunger 128 are separated from the pinch surfaces 134, 136 on anvil body 130 so that the flexible lines 120, 122 are not compressed therebetween. In the open position, heat transfer fluid 94 is permitted to flow at a given flow rate through the lumen 142 of flexible line 120 to the manifold body 55 inside the treatment tip 14 and to flow through the lumen 144 of flexible line 122 out of the manifold body 55. The second position is created when the treatment tip 14 is installed on the nose of the handpiece 12. When the compressive force or pressure applied by the pinch surfaces 134, 136, 138, 140 is removed from the flexible lines 120, 122, the sidewalls of the flexible lines 120, 122 recover approximately to their initial non-compressed state and provide a given flow rate of the heat transfer fluid 94 to the treatment tip 14.

The inlet passage 70 in the stem 62 of the manifold body 55 has a tubular section 152 truncated to terminate at an open end. Similarly, the outlet passage 72 in the stem 62 of the manifold body 55 has a tubular section 154 terminating at another end. The tubular sections 152, 154 are raised above the surrounding portions of the manifold body 55 and project toward the handpiece 12 when the treatment tip 14 is installed to establish a fluid interface with the handpiece 12.

Figure 7:
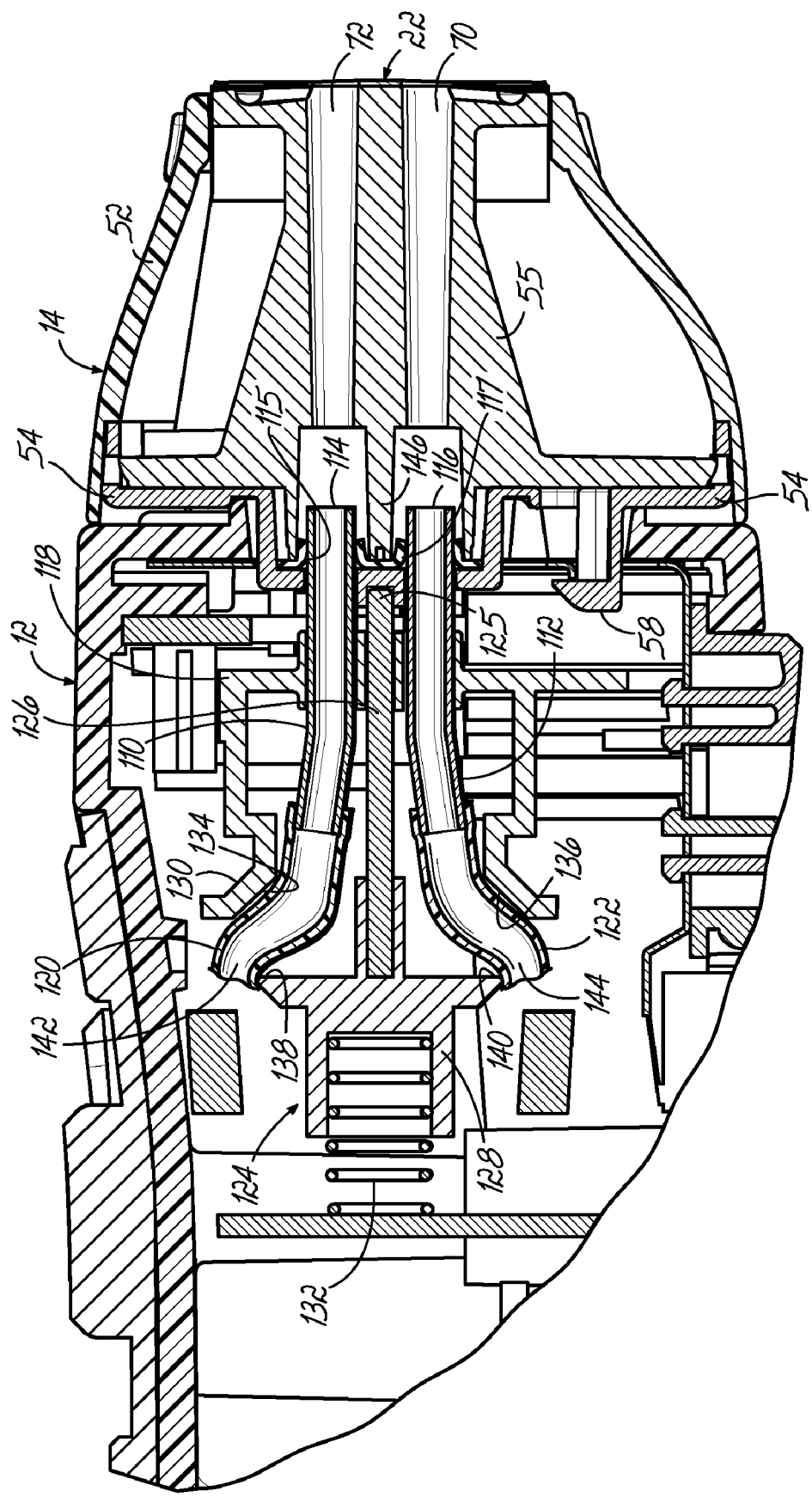
FIG. 7 is an enlarged cross-sectional view of a circled region in FIG. 2.

The tubular sections 152, 154 intersect to define a central activation arm 146. A contact block 145 is located on an opposite side of a septum 150 from the activation arm 146. The contact block 145 and activation arm 146 participate in providing the open position when the treatment tip 14 is installed in the nose of the handpiece 12, as depicted in FIGS. 4 and 7. Specifically, the activation arm 146 and contact block 145, which are self-aligned, are also aligned with the pin 126 of the pinch valve 124. During installation to mate the treatment tip 14 with the handpiece 12, the contact block 145 contacts a portion of the pin 126. The activation arm 146 prevents the septum 150 from deflecting as a reinforcement force is applied by the pin 126 to the contact block 145. The pin 126 and the plunger 128 are pushed by the activation arm 146 and contact block 145 in a direction away from the treatment tip 14 and against the biasing force applied by the coil spring 132 to the plunger 128 that resists motion toward the open position. The coil spring 132 compresses so as to store biasing energy for use in applying a force urging the pinch valve 124 to re-establish the first closed position (FIGS. 8, 9).

The coil spring 132 must apply a spring force to the plunger 128 that is sufficient to compress the flexible lines 120, 122 and place the pinch valve 124 in its closed position. However, the coil spring 132 must readily yield to permit installation of the treatment tip 14 and establish the open position of pinch valve 124. Hence, the properties of the coil spring 132 should be selected to apply an appropriate spring force to the plunger 128.

The flexible lines 120, 122 isolate the heat transfer fluid 94 inside the closed-loop cooling from the components of the pinch valve 124, which prevents contact between the components and the heat transfer fluid 94. The tubing constituting flexible lines 120, 122 is always imposed between the heat transfer fluid 94 and the components of the pinch valve 124, which may be beneficial, for example, if contact with the heat transfer fluid 94 is capable of corroding the components of the pinch valve 124. This benefit means that the materials for the components of the pinch valve 124 are not constrained to be corrosion resistant to the heat transfer fluid 94 as these components are not wetted by the heat transfer fluid 94. Fluid transfer can be effectively controlled by the pinch valve 124 without concerns raised by fluid wetting of the valve components.

Figure 9:
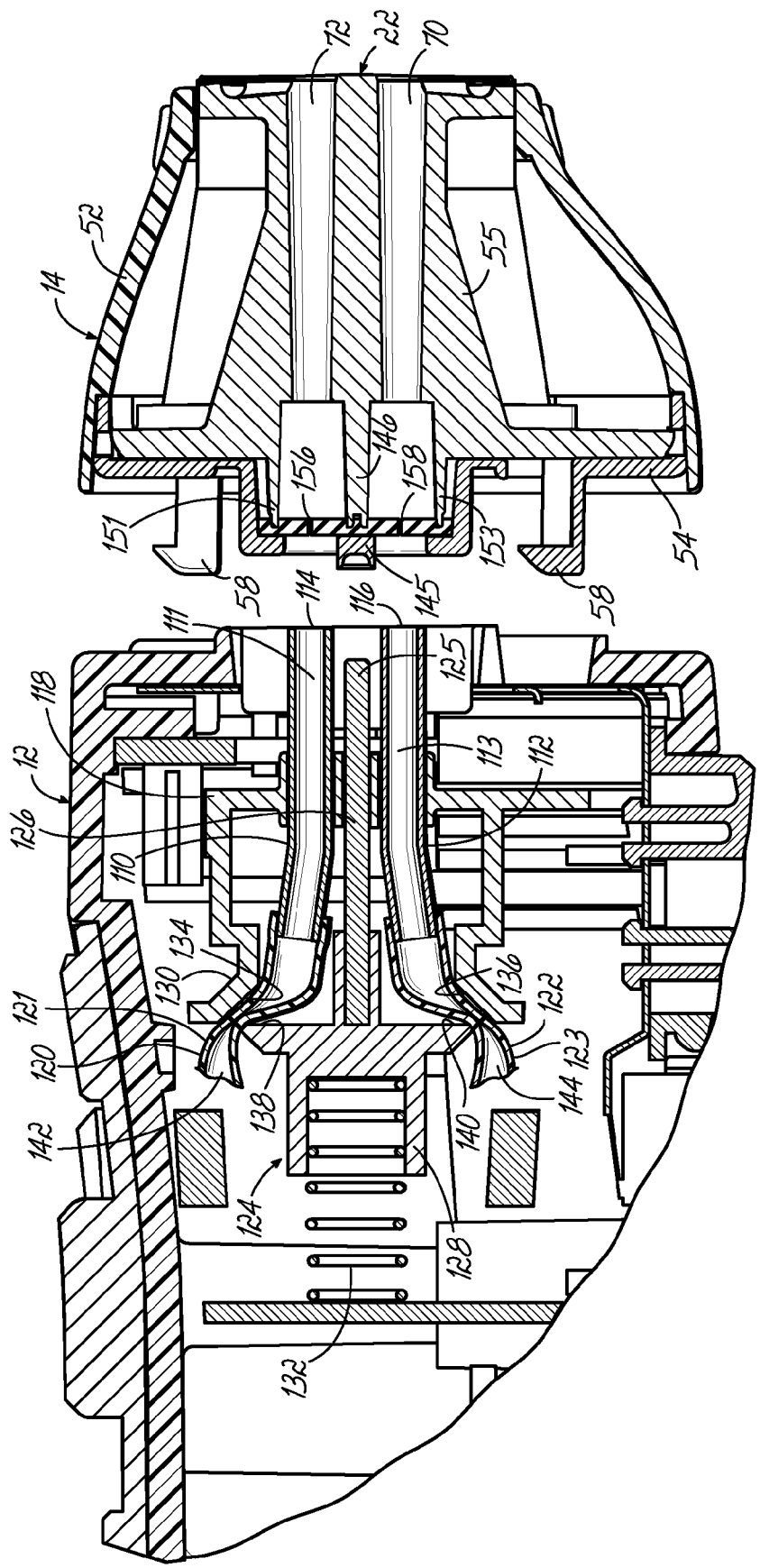
FIG. 9 is an enlarged cross-sectional view similar to FIG. 7 in which the treatment tip is shown separated from the handpiece.

The septum 150, which is best shown in FIGS. 4 and 9, covers the open end 151 of the inlet passage 70 and the open end 153 of the outlet passage 72. During installation, the tips 114, 116 of the rigid tubes 110, 112 apply a force that is substantially perpendicular to the plane of the septum 150. The applied force pierces the septum 150 to define openings 115, 117 that place the lumens 111, 113 of the rigid tubes 110, 112 in fluid communication with the inlet and outlet passages 70, 72, respectively. These temporary fluid connections, which are formed when the treatment tip 14 is attached to the handpiece 12, complete the closed circulation loop. When the treatment tip 14 is separated from the handpiece 12, the septum 150 heals to close or substantially close the openings 115, 117 so that residual heat transfer fluid 94 remaining in the detached treatment tip 14 is blocked from escape.

When the treatment tip 14 is coupled with the handpiece 12, the tip 114 of the rigid tube 110 protrudes through the opening 115 in the septum 150 and projects into an enlarged region at the entrance to the inlet passage 72. Similarly, the tip 116 of the rigid tube 112 protrudes through the opening 117 in the septum 150 and projects into an enlarged region at the entrance to the outlet passage 70. The material of septum 150 about the openings 115, 117 grips the exterior of the tips 114, 116 so that fluid-tight connections are established.

In one embodiment, the septum 150 is a thin membrane composed of an elastomeric material characterized by properties that permit the tips 114, 116 of the rigid tubes 110, 112 to pierce the septum 150 and, upon withdrawal of the tips 114, 116, permit the membrane to heal or close the openings 115, 117 so that residual heat transfer fluid 94 is retained in the treatment tip 14. Specifically, the elastomeric material, when pierced at spaced apart locations by the tips 114, 116 of the rigid tubes 110, 112, near the edges of openings 115, 117 compresses slightly and grips about the outer diameter of each of the rigid tubes 110, 112 with a radial reaction force. When the tips 114, 116 of the rigid tubes 110, 112 are withdrawn, the compressed elastomeric material forces the openings 115, 117 to close. Starter openings 156, 158 are provided in the septum 150 at the approximate locations at which the septum 150 is pierced by the tips 114, 116 of the rigid tubes 110, 112. The starter openings 156, 158 function to permit the tips 114, 116 to initiate penetration through the septum 150 and the formation of openings 115, 117 with a reduced likelihood of either tearing or ripping the septum 150.

In another embodiment, the septum 150 is composed of an elastomeric membrane that is either adhesively bonded with the rear cover 54 or, when the rear cover 54 is integrally formed, with the rear cover 54 by an overmolding process. In yet another embodiment, the septum 150 may be formed from a material having a durometer of about 30 Shore A, as measured by the ASTM D2240 type A scale, and a thickness in a range of about 25 mils to about 35 mils. These combinations of durometer (i.e., the material's resistance to permanent indentation) and thicknesses is believed adequate to impart tear and rip resistance when the tips 114, 116 pierce the septum 150. Other representative materials for septum 150 include, but are not limited to, thermoplastic elastomers (TPEs), such as the DYNAFLEX® family of TPE compounds commercially available from GLS Corporation (McHenry, Ill.).

While the invention has been illustrated by a description of various embodiments and while these embodiments have been described in considerable detail, it is not the intention of the applicant to restrict or in any way limit the scope of the appended claims to such detail. Additional advantages and modifications will readily appear to those skilled in the art. Thus, the invention in its broader aspects is therefore not limited to the specific details, representative apparatus and method, and illustrative example shown and described. Accordingly, departures may be made from such details without departing from the spirit or scope of applicant's general inventive concept.

What is claimed is:

1. An apparatus for treating tissue located beneath a skin surface with high frequency energy, the apparatus comprising:
   a handpiece;
   a treatment tip configured to be removably coupled with the handpiece, the treatment tip including an electrode configured to deliver the high frequency energy to a region of the tissue, a channel for circulating heat transfer fluid proximate to the electrode, and an inlet passage to the channel;
   a first conduit inside the handpiece, the first conduit including a tubular sidewall and a lumen inside the tubular sidewall, the lumen configured to be coupled with the inlet passage for transferring the heat transfer fluid from the handpiece to the inlet passage of the treatment tip; and a septum covering the inlet passage, the septum configured to be pierced by the first conduit to define a first opening for coupling the first conduit with the inlet passage when the treatment tip is coupled to the handpiece and to substantially seal the first opening when the treatment tip is removed from the handpiece to decouple the first conduit from the inlet passage.

2. The apparatus of claim 1 wherein the septum is a membrane composed of an elastomeric material.

3. The apparatus of claim 1 wherein the septum is a membrane composed of a thermoplastic elastomer.

4. The apparatus of claim 1 wherein the septum is a membrane composed of a material having a durometer of about 30 Shore A measured by the ASTM D2240 type A scale and a thickness in a range of about 25 mils to about 35 mils.

5. The apparatus of claim 1 wherein the septum includes a starter opening extending through the septum at a predicted location of the first opening, the starter opening configured to initiate formation of the first opening without tearing the septum.

6. The apparatus of claim 1 wherein the treatment tip includes an outlet passage from the channel, and further comprising:

a second conduit inside the handpiece, the second conduit including a lumen configured to be coupled with the outlet passage for transferring the heat transfer fluid from the inlet passage of the treatment tip to the handpiece.

7. The apparatus of claim 6 wherein the septum covers the outlet passage, and the septum is configured to be pierced by the second conduit to define a second opening to the outlet passage when the treatment tip is coupled to the handpiece and to substantially seal the second opening when the treatment tip is removed from the handpiece.

8. The apparatus of claim 1 wherein the septum is configured to completely seal the first opening when the treatment tip is removed from the handpiece.

9. The apparatus of claim 1 further comprising:

a second conduit inside the handpiece, the second conduit coupled in fluid communication with the first conduit, and the second conduit having a smaller shear modulus than the first conduit; and a flow control valve inside the handpiece, the flow control valve coupled with the second conduit, and the flow control valve configured to occlude the lumen of the second conduit, when the treatment tip is removed from the handpiece, for reducing leakage of the heat transfer fluid from the first conduit.

10. The apparatus of claim 9 wherein the flow control valve is a pinch valve configured to apply a compressive force to the tubular sidewall of the second conduit to control a flow of the heat transfer fluid through the lumen of the first conduit.

11. The apparatus of claim 10 wherein the tubular sidewall of the second conduit is composed of a material with sufficient flexibility to deform to at least partially reduce a cross-sectional area of the lumen, when the compressive force is applied by the pinch valve, and supply the leakage reduction from the first conduit.

12. A method of operating a tissue treatment apparatus to treat tissue located beneath a skin surface with high frequency energy delivered from an electrode, the method comprising:

attaching a treatment tip carrying the electrode to a handpiece to establish a fluid connection between a lumen of a first conduit in the handpiece and an inlet passage in the treatment tip;

piercing a septum with the first conduit, when attaching the treatment tip to the handpiece to establish the fluid connection, to define a first opening permitting the first conduit to be coupled in fluid communication with the inlet passage;

transferring heat transfer fluid through the lumen of the first conduit to the treatment tip; and delivering the high frequency energy from the electrode to a region of the tissue to perform a tissue treatment.

13. The method of claim 12 further comprising:

after delivering the high frequency energy, removing the treatment tip from the handpiece; and when the treatment tip is removed from the handpiece, resiliently closing the first opening in the septum.

14. The method of claim 12 wherein delivering the high frequency energy further comprises:

transmitting the high frequency energy from the electrode through a dielectric substrate by capacitive coupling with the region of the tissue.

15. The method of claim 12 further comprising:

when the treatment tip is attached to the handpiece, establishing a fluid connection between a lumen of a second conduit in the handpiece and an outlet passage in the treatment tip;

piercing the septum with the second conduit, when attaching the treatment tip to the handpiece, to define a second opening permitting the second conduit to be coupled in fluid communication with the outlet passage; and transferring the heat transfer fluid through the lumen of the second conduit from the treatment tip to the handpiece.

16. The method of claim 15 further comprising:

removing the treatment tip from the handpiece so that the each of the first and second conduits has an open end; and when the treatment tip is removed from the handpiece, at least partially occluding the lumen of the first conduit and the lumen of the second conduit so that a negligible amount of the heat transfer fluid leaks from the open end of the first conduit and the open end of the second conduit.

17. The method of claim 16 wherein the occlusion of the lumens of the first and second conduits occurs concurrently.

18. The method of claim 12 further comprising:

removing the treatment tip from the handpiece so that the first conduit has an open end; and when the treatment tip is removed from the handpiece, at least partially occluding the lumen of the first conduit so that a negligible amount of the heat transfer fluid leaks from the open end of the first conduit.

* * * * *

UNITED STATES PATENT AND TRADEMARK OFFICE
CERTIFICATE OF CORRECTION

| | | |
|---|---|---|
| PATENT NO. | : 8,121,704 B2 | |
| APPLICATION NO. | : 12/142104 | |
| DATED | : February 21, 2012 | |
| INVENTOR(S) | : Alan Schenck | |

It is certified that error appears in the above-identified patent and that said Letters Patent is hereby corrected as shown below:

In the Specification:

At column 4, line number 11, after "deposited", insert --on--.

At column 10, line number 35, change "is" to --are--.

In the Claims:

At column 12, claim number 16, line number 41, after "that", delete "the".

Signed and Sealed this
Tenth Day of April, 2012

David J. Kappos
*Director of the United States Patent and Trademark Office*